(12) United States Patent
Nazer et al.

(10) Patent No.: US 12,343,000 B1
(45) Date of Patent: Jul. 1, 2025

(54) STERNOTOMY RETRACTOR SYSTEM

(71) Applicant: KING SAUD UNIVERSITY, Riyadh (SA)

(72) Inventors: Rakan Ibrahim Nazer, Riyadh (SA); Nabeel Ahmed Ali, Riyadh (SA); Ali Mufraih Albaratti, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/088,694

(22) Filed: Mar. 24, 2025

(51) Int. Cl.
*A61B 17/02* (2006.01)

(52) U.S. Cl.
CPC .................................. *A61B 17/02* (2013.01)

(58) Field of Classification Search
CPC ........................... A61B 17/02; A61B 17/0218
See application file for complete search history.

(56) References Cited

U.S. PATENT DOCUMENTS

| | | |
|---|---|---|
| 1,309,734 A | 7/1919 | Hemfling |
| 1,389,820 A | 9/1921 | Andrew |
| 4,151,838 A * | 5/1979 | Crew ...................... A61B 17/02 606/1 |
| 4,459,985 A | 7/1984 | McKay et al. |
| 4,934,352 A | 6/1990 | Sullivan, Jr. |
| 5,447,289 A | 9/1995 | Callahan |
| 5,474,094 A | 12/1995 | Ellenberg, III |
| 5,795,291 A | 8/1998 | Koros et al. |
| 5,846,187 A | 12/1998 | Wells et al. |
| 8,529,444 B2 * | 9/2013 | Hale ...................... A61B 17/02 600/206 |
| 8,668,697 B2 | 3/2014 | Deslauriers et al. |

FOREIGN PATENT DOCUMENTS

EP 1498074 B1 6/2011

* cited by examiner

*Primary Examiner* — Si Ming Ku
(74) *Attorney, Agent, or Firm* — Nath, Goldberg & Meyer; Joshua B. Goldberg

(57) ABSTRACT

The present subject matter relates to a sternotomy retractor system, comprising a first device portion and a second device portion, each of the first device portion and the second device portion including a base assembly, including a first base portion including a groove extending along an edge thereof, a second base portion including a groove extending along an edge thereof, and a handle. The first and second base portions are removably connected and the handle slidably engages the groove of the first and second base portions when the first and second base portions are connected together.

15 Claims, 4 Drawing Sheets

STERNOTOMY RETRACTOR SYSTEM

BACKGROUND

1. Field

The disclosure of the present patent application relates to a surgical tool and, particularly, to a sternotomy retractor system for redo sternotomies.

2. Description of the Related Art

Redo sternotomy is a common but high-risk procedure in cardiac surgery. Due to the presence of adhesions and proximity of the heart to the sternum in such cases, the risk of cardiac and vascular injury during re-entry is significant. Existing tools fail to adequately address the dual needs of safe sternum elevation and clear surgical access. Existing tools often have a bar connecting the arms on the device and the bar extends across the open area of the surgical site blocking both the view of the medical providers and the path of the saw and other surgical instruments.

Thus, a new sternotomy retractor system that decreases these challenges is desired.

SUMMARY

The present subject matter relates to a sternotomy retractor system designed for use during redo sternotomy procedures in cardiac surgery. Specifically, it provides a mechanism to safely elevate the sternum, minimizing the risk of damage to the heart, major vascular structures, and other intrathoracic tissues during re-entry into the chest cavity. The retractor system described herein bridges the gap between current devices by providing a specialized mechanism to lift and maintain the sternum in an elevated position while ensuring stability and precision.

The present subject matter relates to a sternotomy retractor system. The sternotomy retractor system includes a first device portion and a second device portion. Each device portion includes a base assembly, including a first base portion and a second base portion. The first base portion may be configured to receive two bolts extending from the second base portion. A free end of each bolt can threadedly engage a knob. The sternotomy retractor system may also include a handle slidably and removably coupled to the base assembly in a space between the first portion and the section portion of the device.

The handle 4 includes a generally rectangular bar having a first portion and an second portion extending from the first portion. In an embodiment, the second portion extends at an angle of about 135 degrees from the first portion. A guide extends perpendicular to one end of the bar and a grip is coupled to an opposing end of the bar. The grip can be generally oval-shaped having a smooth portion and an indented portion opposite the smooth portion. The indented portion includes scallops or indents for receiving the fingers of a user. The handle and grip are designed to be ergonomical for easy manipulation and positioning of the device.

The present subject matter also relates to a method of lifting a sternum in a patient using the sternotomy retractor system described herein. The method may include making an incision over a previous sternotomy scar in the patient to expose an upper table of the sternum bone by dissecting skin and subcutaneous tissues. The method may also include unraveling sternal wires from a previous sternotomy. The sternotomy wires may be unraveled on both sides of the sternum. The handle of the sternotomy retractor system may be attached to the base assembly of the sternotomy retractor system and free ends of the sternotomy wires may be clasped between the first portion and second portion of the base assembly on both sides of the sternum. The two knobs can be tightened to secure the base assembly to the sternum. The method may then include lifting the sternum away from underlying structures using the handle of the sternotomy retractor system. Anterior and posterior sternal tables may be cut using a redo oscillating saw. The method may then include removing the sternotomy wires and performing retrosternal dissection using a tool selected from the group consisting of electrocautery and sharp dissection. The method may then include dividing and lifting the sternum and maintaining the sternum in an elevated position using the sternotomy retractor system.

These and other features of the present subject matter will become readily apparent upon further review of the following specification.

DETAILED DESCRIPTION OF THE PREFERRED EMBODIMENTS

Figure 1:
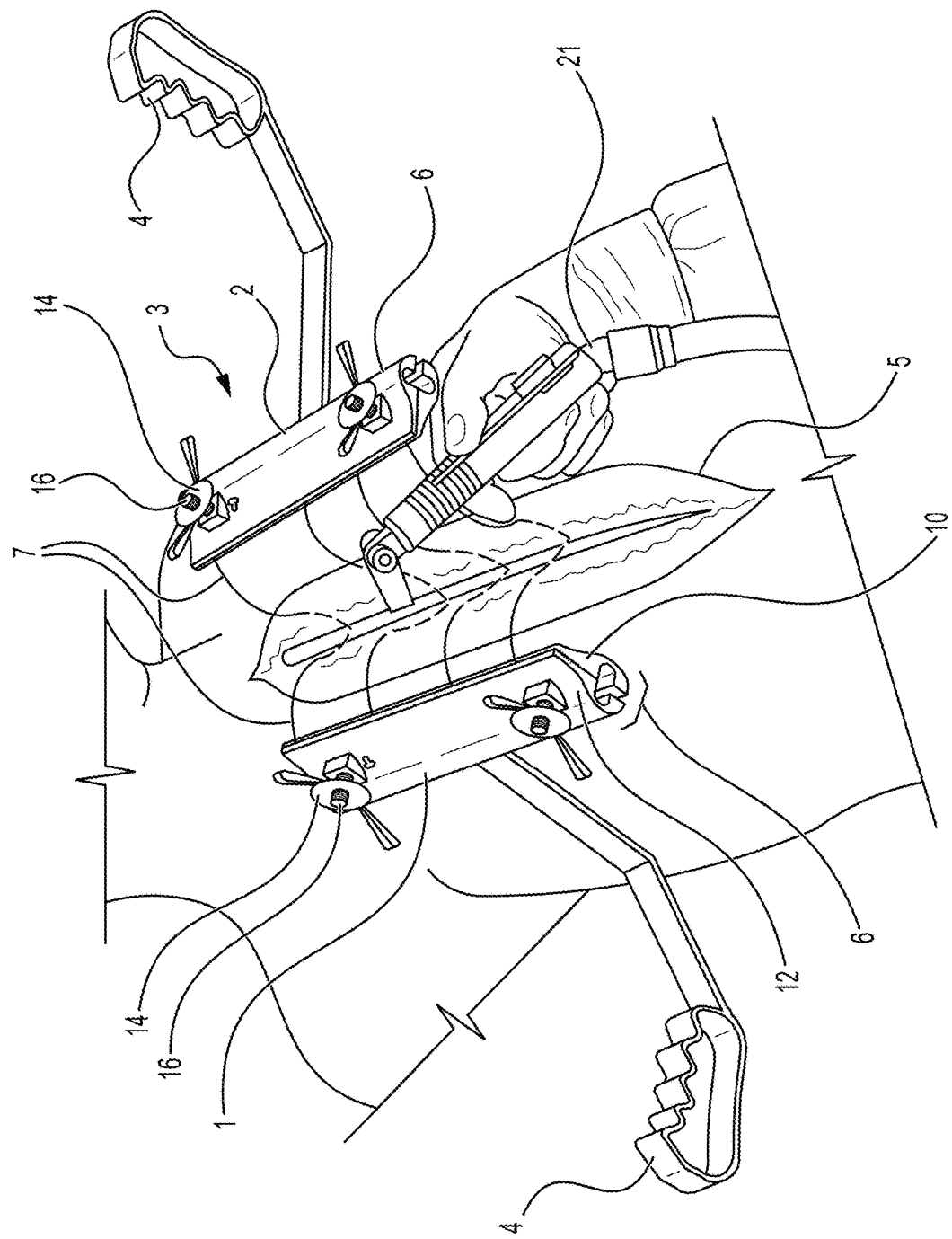
FIG. 1 shows a top view of an embodiment of a sternotomy retractor system, as described herein, in use lifting sternotomy wires during open heart surgery.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as heart disease, other heart related conditions, and conditions of body parts or organs protected by the sternum.

The present subject matter relates to a specialized sternotomy retractor system providing a mechanism to lift and maintain the sternum of a patient in an elevated position while ensuring stability and control. The sternotomy retractor system described herein may provide enhanced safety by reducing the risk of injury to the heart and adjacent structures during redo sternotomy procedures. The sternotomy retractor system may also improve visibility and access to the surgical site for the surgeon and other medical professions by elevating the sternum to create a clearer field for surgical intervention. The sternotomy retractor system may have increased ease of use over previous sternotomy retractor systems used in sternotomies due to the ergonomic design and precision control features of the device which may allow for a smooth operation by the surgical team. The device may be highly adaptable by providing a modular design which may permit customization based on specific surgical needs and specific patient anatomy.

Referring to FIG. 1, a sternotomy retractor system 3 for sternotomy procedures in use is illustrated. As illustrated, the sternotomy retractor system 3 includes a first device portion 1 and a second device portion 2 that may be used together during a surgical procedure. The first device portion 1 and the second device portion 2 are identical. In an embodiment, the first and second device portions 1, 2 include ergonomic handles 4 which are slidably coupled to a respective base assembly 6.

In an embodiment, the base assembly 6 of each of the first and second device portions 1,2 includes a first base portion 10 and a second base portion 12. As the first device portion 1 and the second device portion 2 are identical, the base assembly 6 of only the first device portion 1 is described in detail herein. In an embodiment, the handle 4 attached to the first device portion 1 can be slidably received within groove 9 of the first base portion 10 and within groove 8 of the second base portion 12. The sternotomy retractor system 3 may be used to clamp the sternotomy wires and to lift the sternum. The handles 4 may slide during use of the device allowing synchronized movement with a redo oscillating saw which may allow for seamless sternum division.

In an embodiment, the sternotomy retractor system 3 may be used during a sternotomy procedure. The procedure may include making a skin incision 5 over a previous sternotomy scar of a patient. Skin and subcutaneous tissues of the patient may be dissected to expose an upper table of the sternal bone. Sternal wires 7 from a previous sternotomy procedure may be unraveled on both sides of the sternum. Free ends of the wires 7 may be clasped or clamped between the first base portion 10 and the second base portion 12 of the base assembly 6. The base assembly 6 of the device may be attached to the sternum and positioned securely. One or more handles 4 may be coupled to the base assembly 6 and secured using the knobs 14. In an embodiment, the knobs 14 may be twisted to tighten bolts 16 and secure the first base portion 10 and the second base portion 12 together. Then, a surgical assistant may use the handles 4 to elevate the sternum away from underlying vital structures such as by non-limiting example, the heart and great vessels. A redo oscillating saw 18 may then be introduced. In other implementations, other suitable surgical cutting devices may be used. The redo oscillating saw 18 may be used to cut through the anterior and posterior sternal tables of the patient. The handles 4 of the sternotomy retractor system 3 allow the base assembly 6 to lift and slide in alignment with the saw 18. This may facilitate a smooth division of the sternum in each individual segment.

After the posterior sternal table is cut and divided, the sternotomy wires 7 may be removed to prevent interference with the surgical field. Rectrosternal dissection can then be performed using electrocautery or sharp dissection which minimize upward traction and avoid injury to critical structures. If adhesions are dense, the pleura may be intentionally entered to allow mediastinal structures to fall away from the sternum which may help to reduce tension. Once the sternum is fully divided and lifted, the sternotomy retractor system 3 maintains the elevation throughout the procedure, ensuring optimal visibility and access for the surgeon.

Figure 2:
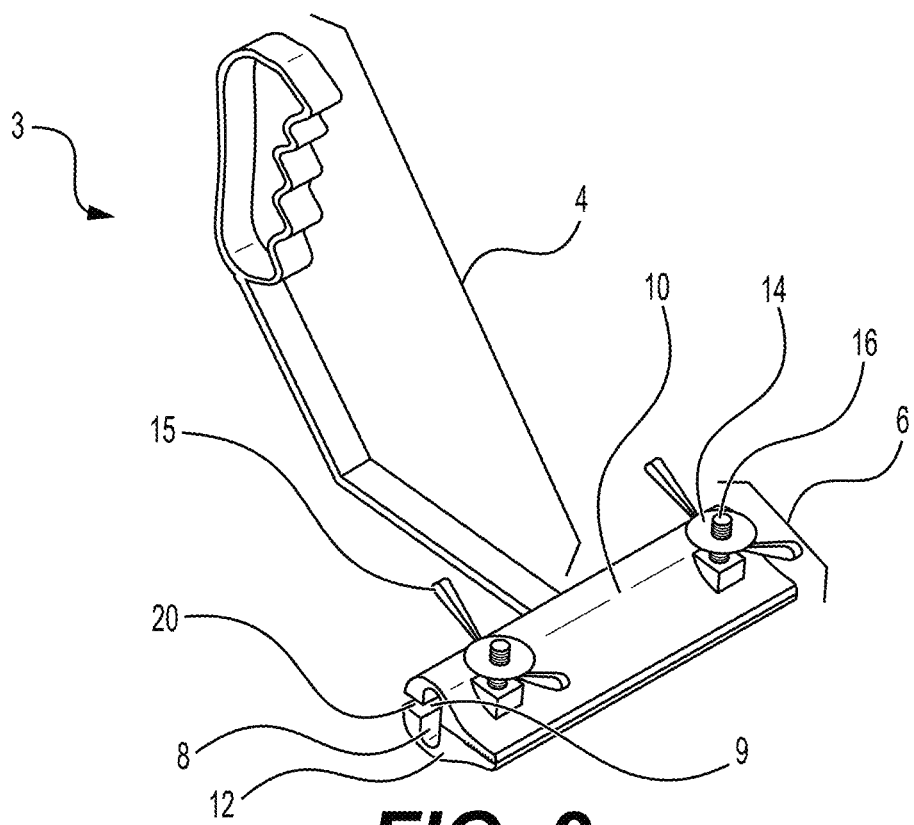
FIG. 2 shows a perspective view of an embodiment of a sternotomy retractor system as described herein having one handle.

Referring to FIG. 2, a perspective view of the first portion 1 of the sternotomy retractor system 3 is illustrated. In this figure, the first portion 1 of device 3 is fully assembled. The device 3 is designed with modular components, including the first base portion 10 and the second base portion 12 of base assembly 6, handles 4 which act as lifting arms, and knobs 14 that removably couple with bolts 16 extending from the second base portion 12 of the base assembly 6. Some parts may be preassembled before surgery for efficiency. Final adjustments and assembly may be done at the surgical site to ensure proper positioning based on the patient's anatomy.

Figure 3:
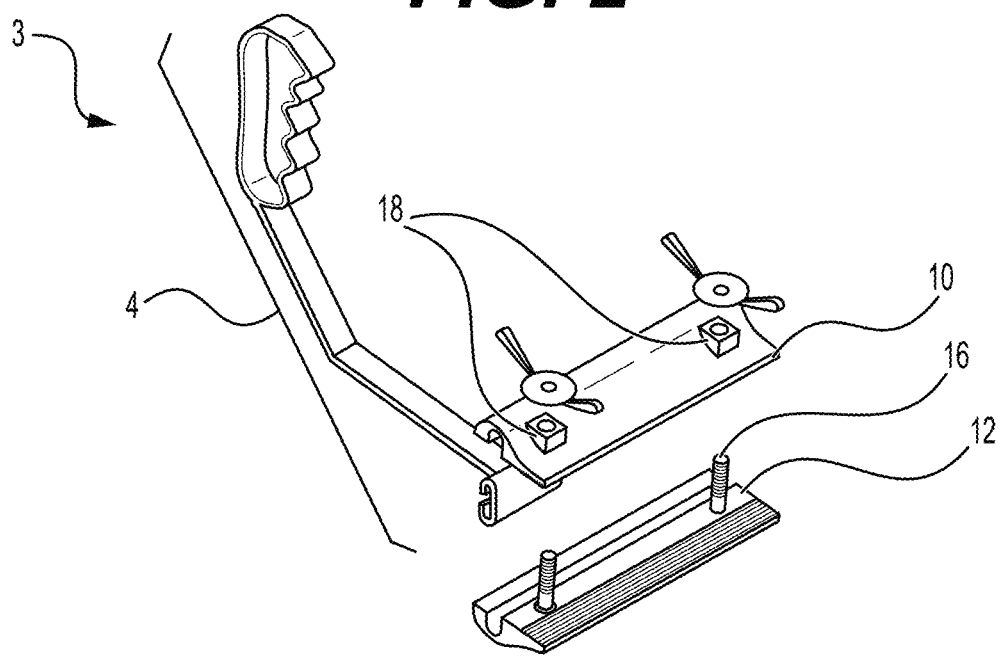
FIG. 3 is an exploded view of an embodiment of a sternotomy retractor system as described herein.
Figure 4:
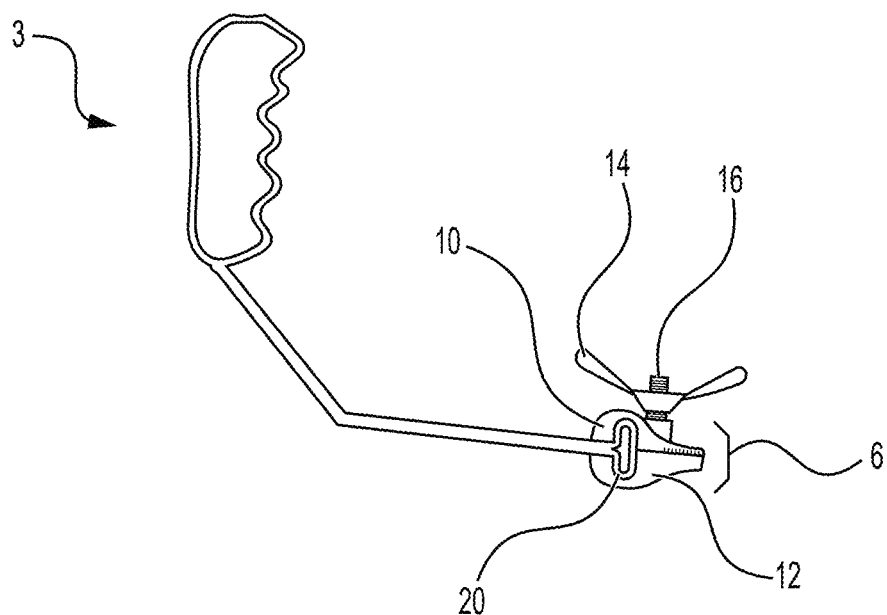
FIG. 4 is a side view of an embodiment of a sternotomy retractor system as described herein.

Referring now to FIG. 3, an exploded view of the first device portion 1 is illustrated. The first device portion 1 includes a base assembly 6 including a first base portion 10 and a second base portion 12. The first base portion 10 has two holes 18 defined therethrough for receiving two bolts 16 extending from the second base portion 12. The base frame assembly 6 provides a stable structure for securing the device 3 during surgery. A side view of the sternotomy retractor system 3 is illustrated in FIG. 4.

Figure 8:
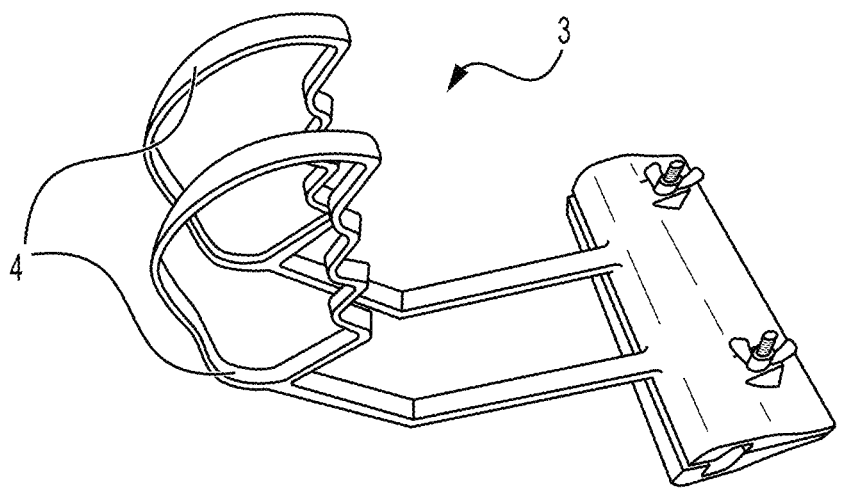
FIG. 8 is a top view of an embodiment of a sternotomy retractor system having two handles coupled with the base assembly.

The assembly 6 of the first device portion 1 slidably and removably engages handle 4 in a space 20 between the first base portion 10 and the second base portion 12. The space 20 between the first base portion 10 and second base portion 12 is created by the grooves 8 and 9 in each of the first base portion 10 and the second base portion 12. The sliding of the handle 4 allows for linear lifting of sternal wires in synchronous movement with an oscillating saw. This may allow for better precision and less likelihood of injury from a saw during redo opening of the sternum. In various embodiments, each of the first and second device portions 1,2 of the sternotomy retractor system 3 may include two handles 4 as illustrated in FIG. 8.

Figure 5:
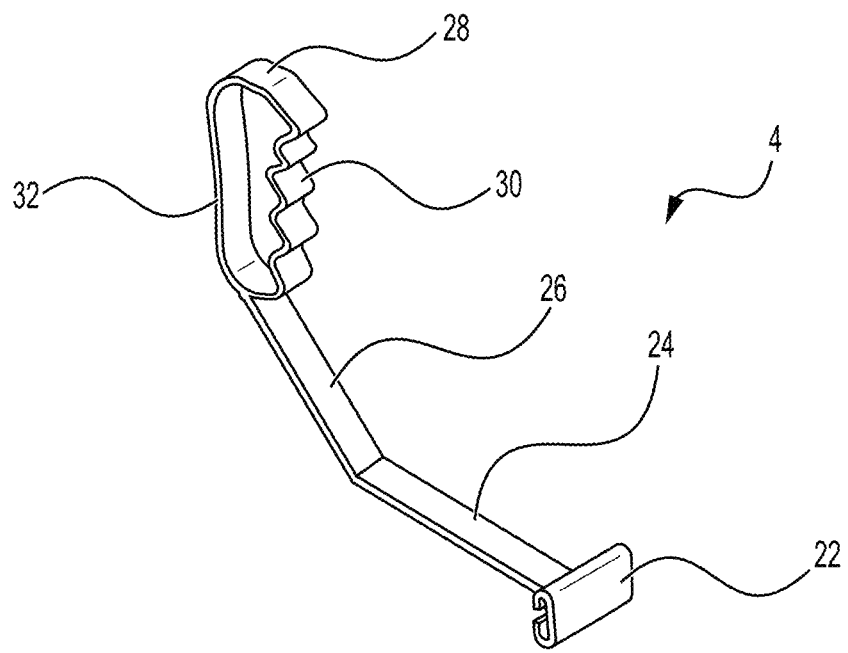
FIG. 5 is a side view of an embodiment of a handle of the sternotomy retractor system as described herein.

Referring to FIG. 5, the handle 4 includes a generally rectangular bar having a first portion 24 and a second portion 26 extending from the first portion 24. In an embodiment, the second portion 26 extends at an angle of about 135 degrees from the first portion 24. A guide 22 extends perpendicular to an end of the first portion 24 and a grip 28 extends from an end of the second portion 26. The grip 28 can be generally ring-shaped having a smooth portion 32 and an indented portion 30 opposite the smooth portion 32. The indented portion 30 includes scallops or indents for receiving the fingers of a user. The handle 4 and grip 28 are designed to be ergonomical for easy manipulation and positioning of the device.

Referring again to FIG. 3, the first device portion 1 of the sternotomy retractor system 3 includes two knobs 14 and 15 configured to removably couple with, e.g., threadedly engage, the bolts 16 extending from the second base portion 12 of the base assembly 6. The knobs 14 and 15 may allow for fine adjustment to facilitate the gradual and controlled lifting of the sternum in a patient which may ensure safety and precision and prevent sudden movement or excessive force from the sternotomy retractor system 3. These may reduce the risk of injury to the patient.

Figure 6:
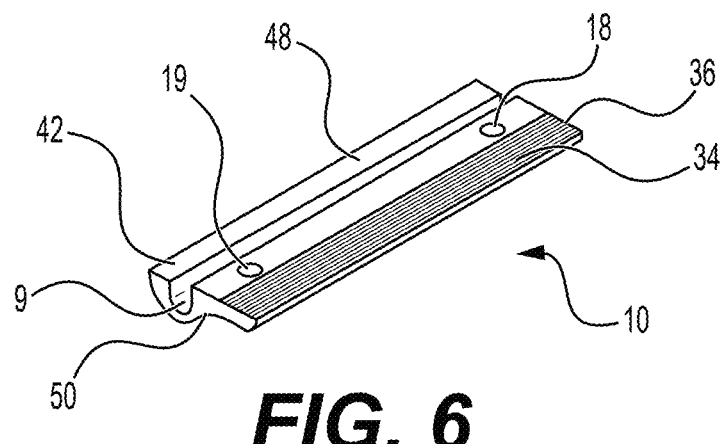
FIG. 6 is a perspective view of an embodiment of a first portion of a base assembly of the sternotomy retractor system as described herein.
Figure 7:
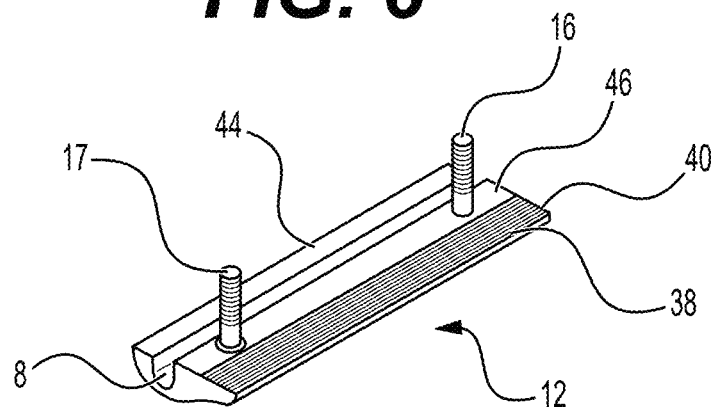
FIG. 7 is a perspective view of an embodiment of a second portion of a base assembly of the sternotomy retractor system as described herein.

Referring to FIG. 6, the first base portion 10 includes a grid structure 34 on a first edge 36 thereof. The second base portion 12 includes grid structure 38 on a first edge 40 thereof, as illustrated in FIG. 7. The grid structure 34 may include teeth-like structures which are configured to clamp sternotomy wires when combined with grid structure 38 of the second base portion 12. As previously described, the first portion 10 includes groove 9 on a second edge 42 of the first portion 10 which is opposite the first edge 36 of the first portion 10. The groove 9 is configured to receive the guide 22 of the handle 4 of the sternotomy retractor system 3 when combined with a groove 8 on a second edge 44 of the second portion 12 of the base assembly.

In various embodiments, the sternotomy retractor system may include a safety mechanism which is configured to limit or prevent overextension of the device 3.

In various embodiments, the device is sterilizable. The device may be formed of a material that can be sterilized such as, by non-limiting example, a metal selected from the group consisting of surgical grade stainless steel, tungsten carbide, titanium, nitinol, niobium, platinum, and palladium.

In various embodiments, the device may be adaptable to different surgical procedures or scenarios such as by non-limiting example In various embodiments, the device is configured to clamp sternotomy wires.

Referring again to FIG. 1, the sternotomy retractor system may be used in a method of lifting a sternum in a patient. The method may include making an incision 5 over a previous sternotomy scar in the patient and exposing an upper table of the sternum bone by dissecting skin and subcutaneous tissues. The method may further include unraveling sternal wires 7 from previous sternotomy. The sternotomy wires 7 may be unraveled on both sides of the sternum. The method may include clasping free ends of the sternotomy wires between the first portion 10 and second portion 12 of the base assembly 4 on both sides of the sternum, attaching the handle 4 of the sternotomy retractor system 3 to the base assembly 6 of the sternotomy retractor system 3, and attaching the base assembly 6 to the sternum. The two knobs 14 and 15 of the device 3 may be tightened to secure the base assembly 4. Once the base assembly 4 is secured, the sternum may be lifted away from underlying internal structures of the patient using the handle 4 of the sternotomy retractor system 3. Once the sternum is lifted, the method may include cutting through the anterior and posterior sternal tables using a redo oscillating saw 18.

The method may then include removing the sternotomy wires 7. After the sternotomy wires 7 are removed, the method may include performing a retrosternal dissection. The retrosternal dissection may be performed using one tool selected from the group consisting of electrocautery and sharp dissection. The method may include dividing and lifting the sternum and maintaining the sternum in an elevated position using the sternotomy retractor system 3.

In other embodiments, the method may further include sliding the handles of the sternotomy retractor system in alignment with the movement of the saw.

In still other embodiments, the underlying structures may include a heart of the patient and vessels of the patient.

An embodiment of the present subject matter relates to a sternotomy retractor kit. The sternotomy retractor kit may include two base assemblies 6. Each base assembly 6 may include a first base portion 10 and a second base portion 12. The second base portion 12 may include two bolts 16 extending from a surface 46 of the second portion 12. The first base portion 10 may include two holes 18 and 19 extending from a first surface 48 to a second surface 50 of the first base portion 10. Each of the first base portion 10 and the second base portion 12 may include a grid structure 34 and 38 on a first edge 36 of the first base portion 10 and a first edge 38 of the second base portion 12. The first base portion 10 and second base portion 12 may also each include a groove 9 and 8 on a second edge 42 of the first base portion 10 and a second edge 44 of the second base portion 12.

The kit may include two handles 4. Each handle 4 can include a guide 22 perpendicularly coupled with a first end of a first portion 24. The handle 4 may also include an second portion 26, wherein a first end of the second portion 26 is coupled with a second end of the first portion 24. The handle 4 may include a grip 28 coupled with the second end of the second portion 26. The grip 28 may include an indented portion having finger grips 30 opposite a smooth portion 32. The kit may include four knobs 14 and 15 configured to removably couple with the bolts 16 and 17.

In further embodiments, the device may be made of a metal selected from the group consisting of surgical grade stainless steel, tungsten carbide, titanium, nitinol, niobium, platinum, and palladium.

In other embodiments, the device may be adaptable to different surgical scenarios.

In another embodiment, the device may be sterilizable.

In still other embodiments, the sternotomy retractor system may be configured to clamp sternotomy wires.

It is to be understood that a sternotomy retractor system for sternotomy procedures described herein are not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sternotomy retractor system, comprising:
   a first device portion and a second device portion, each of the first device portion and the second device portion including:
   a base assembly, including a first base portion including a groove extending along an edge thereof, a second base portion including a groove extending along an edge thereof, and a handle, the first and second base portions being removably connected, the handle slidably engaging the groove of the first and second base portions when the first and second base portions are connected together.

2. The retractor system of claim 1, wherein the first base portion includes a pair of holes defined therethrough, the second base portion includes a pair of bolts extending therefrom, the holes being configured for the receiving bolts extending from the second base portion.

3. The retractor system of claim 1, wherein the handle includes a generally rectangular bar having a first portion, a second portion extending from the first portion, a guide extending perpendicular to an end of the first portion, and a grip extending from an end of the second portion.

4. The retractor system of claim 3, wherein the second portion extends at an angle of about 135 degrees from the first portion.

5. The retractor system of claim 3, wherein the handle slidably and removably engages the base assembly between the first base portion and the second base portion.

6. The retractor system of claim 3, wherein the grip includes an indented portion including scallops for receiving the fingers of a user.

7. The retractor system of claim 1, wherein the first and second base portions include a grid structure along edge portions thereof.

8. A sternotomy retractor system, comprising:
   a first device portion and a second device portion, each of the first device portion and the second device portion including:
   a base assembly, including
   a first base portion including a pair of holes defined therethrough and a groove extending along an edge portion thereof,
   a second base portion removably coupled to the first base portion, the second base portion including a pair of bolts and a groove extending along an edge thereof, the bolts configured for removably engaging the holes of the first base portion, and
   a handle between the first base portion and the second base portion, the handle slidably positioned within the grooves of the first and second base portions.

9. The retractor system of claim 8, wherein the handle includes a generally rectangular bar having a first portion, a second portion extending from the first portion, a guide extending perpendicular to an end of the first portion, and a grip extending from an end of the second portion.

10. The retractor system of claim 9, wherein the second portion extends at an angle of about 135 degrees from the first portion.

11. The retractor system of claim 9, wherein the grip includes an indented portion including scallops for receiving the fingers of a user.

12. The retractor system of claim 8, wherein the first and second base portions include a grid structure along edge portions thereof.

13. A sternotomy retractor kit, comprising two base assemblies, each base assembly including
   a first base portion including a pair of holes defined therethrough and a groove extending along an edge portion thereof,
   a second base portion removably coupled to the first base portion, the second base portion including a pair of bolts and a groove extending along an edge thereof, the bolts configured for removably engaging the holes of the first base portion,
   a handle between the first base portion and the second base portion, the handle slidably positioned within the grooves of the first and second base portions.

14. The sternotomy retractor kit of claim 13, wherein the handle includes a generally rectangular bar having a first portion, a second portion extending from the first portion, a guide extending perpendicular to an end of the first portion, and a grip extending from an end of the second portion.

15. The sternotomy retractor kit of claim 13, wherein the second portion extends at an angle of about 135 degrees from the first portion.

* * * * *